United States Patent [19]

Rosenberg

[11] 4,326,957
[45] Apr. 27, 1982

[54] VENTED FILTER SPIGOT FOR INTRAVENOUS LIQUID ADMINISTRATION APPARATUS

[75] Inventor: David J. Rosenberg, Glen Cove, N.Y.

[73] Assignee: Pall Corporation, Glen Cove, N.Y.

[21] Appl. No.: 8,659

[22] Filed: Feb. 2, 1979

Related U.S. Application Data

[63] Continuation-in-part of Ser. No. 926,766, Jul. 21, 1978, Pat. No. 4,177,149.

[51] Int. Cl.³ .................... B01D 35/02; B01D 19/00
[52] U.S. Cl. .................................. 210/436; 210/472; 210/927; 210/446; 55/159
[58] Field of Search ............... 210/927, 472, 446, 436; 55/159, 318

[56] References Cited

U.S. PATENT DOCUMENTS 3,803,810  4/1974  Rosenberg ........................ 55/159
4,116,646  9/1978  Edwards ........................... 210/927
4,190,426  2/1980  Roschke ........................... 210/927

*Primary Examiner*—John Adee

[57] ABSTRACT

A vented filter spigot for gravity feed intravenous liquid administration is provided having a filter spigot housing; a filter chamber in the housing; an inlet and an outlet in the housing, the housing being arranged to have the inlet oriented up and the outlet oriented down when installed for liquid feed from a liquid supply for intravenous administration; the inlet being shaped for attachment to a supply of liquid in a container for intravenous administration, and the outlet being shaped for attachment to an intravenous liquid administration apparatus; a liquid-permeable filter that is gas-impermeable when wet disposed in the filter chamber in a manner so as to extend generally vertically when the inlet is oriented up, and across the line of fluid flow through the chamber from the inlet to the outlet so that all through flow must pass through the filter; and dividing the chamber into two generally vertically-extending portions, one upstream and one downstream of the filter; a vent in an uppermost portion of the housing when the inlet is oriented up in flow communication with the upstream portion of the filter chamber; and a liquid-impermeable gas permeable filter disposed across the line of flow through the vent, so that all vent flow must pass through the filter, the filter restricting such flow to gas to which it is permeable; first and second passages in the housing putting the inlet into fluid flow communication with the filter chamber, the first passage opening into an upper part of the upstream portion of the filter chamber, and the second passage being longer than the first and opening into a lower part of the upstream portion of the filter chamber; whereby outflow of liquid via the filter chamber through the outlet aspirates air via the vent, liquid-impermeable gas-permeable filter and first passage into the container holding the supply of liquid, and makes it possible to maintain liquid flow from the container via the second passage to the outlet.

12 Claims, 3 Drawing Figures

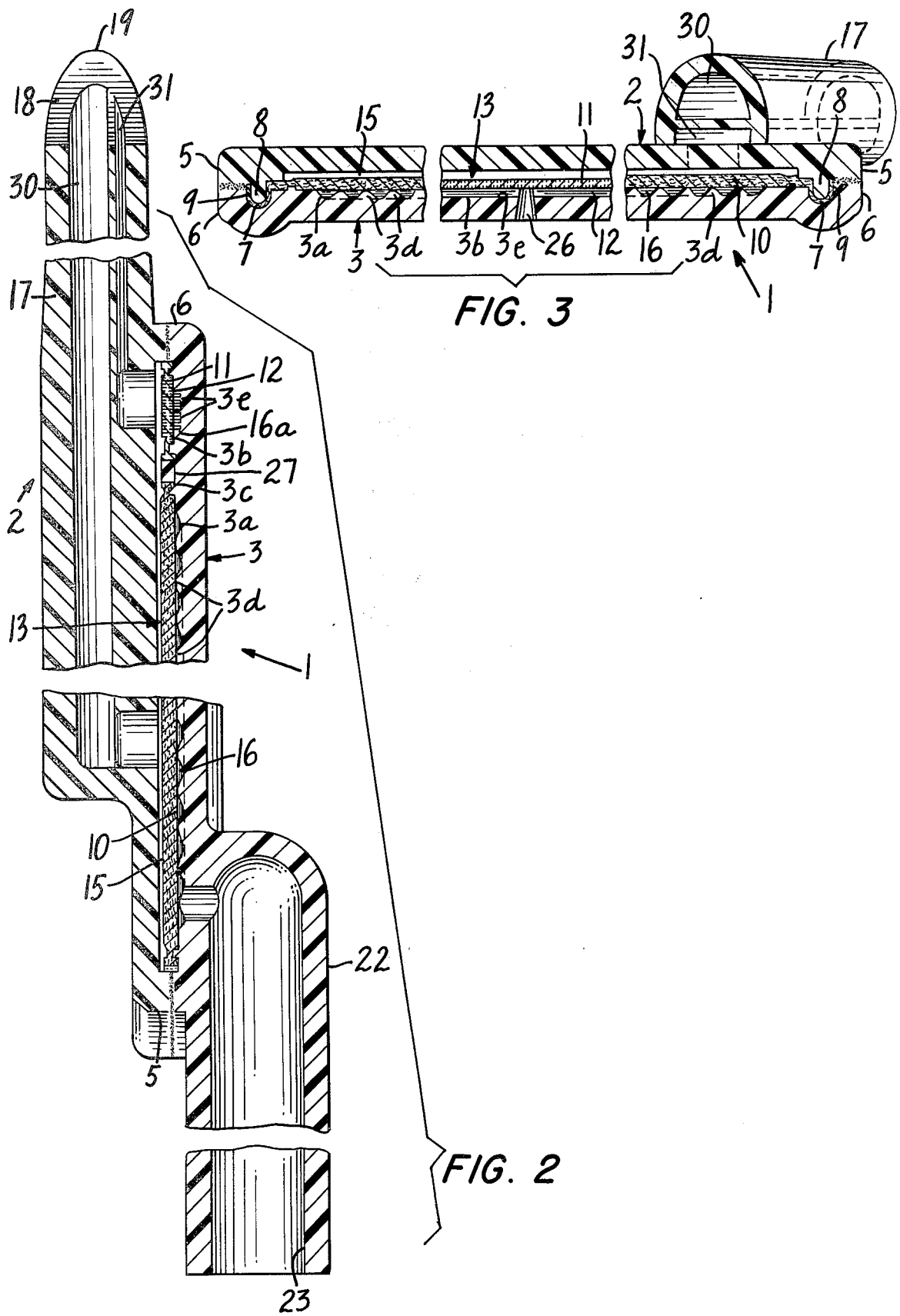

VENTED FILTER SPIGOT FOR INTRAVENOUS LIQUID ADMINISTRATION APPARATUS

This application is a continuation-in-part of Ser. No. 926,766 filed July 21, 1978, now U.S. Pat. No. 4,177,149 patented Dec. 4, 1979.

In many types of medical treatment, such as blood transfusions, intravenous feeding, and the like, it is necessary to introduce into a patient liquid from a liquid supply, sometimes in rather large amounts. When this is done, it is quite important that absolutely no contaminant be permitted to pass into the patient with the liquid, because of the danger of injury or infection, or of an embolism, with possibly fatal consequences. Before such an injection usually can be carried forward, therefore, it is necessary to clear the line from the supply to the patient of air, and exclude air from the system thereafter. This is not easy to do, however. There is the further problem, if the liquid supply is held in a rigid-walled container, with gravity feed, that air must be admitted into the container as liquid is removed, to prevent the building up of a vacuum in the container which slows and eventually halts liquid flow. This air must be freed of contaminants before it can be allowed to enter the container, and so leakage of air into the system has to be prevented.

Accordingly, in gravity feed systems there is the constant danger that air can enter the system during administration, since the system can hardly be easily assembled and disassembled, and still be completely air-tight, and there is also the possibility of human error in such assembly. The danger increases if a large volume of fluid is to be injected. If the reservoir runs dry, there is also again a danger that air will be injected, especially when the liquid is being injected under pressure, using, for instance, a mechanical pump.

Intravenous liquid administration apparatus accordingly requires a gas vent and both a gas filter across this vent and a liquid filter to ensure that undesirable or foreign contaminants in gaseous or particulate form not be administered intravenously, with untoward consequences.

In order to introduce air into the container, it is customary to provide a vented filter spigot with two fluid flow passages, having a gas filter across one vented passage through which air is drawn into the container via the spigot as liquid is withdrawn from the container via the other passage. Liquid flow through this spigot passage is not filtered, however. A separate filter assembly has to be provided, if the liquid is to be filtered.

Many types of intravenous liquid filter assemblies have been provided, of which the system described in Barr et al U.S. Pat. No. 3,557,786 patented Jan. 26, 1971 is exemplary. The filter is usually disposed in an intravenous liquid drip chamber attached to the supply of liquid to be administered, in such a manner that the filter is integral with the chamber housing, all flow through the chamber having to pass through the filter before it can be administered. Such filter assemblies are intended to be disposed of after one use, and to meet the requirement of disposability, the device must be simple and inexpensive to manufacture.

A filter having small pores is incapable of passing gases at fluid pressures below the so-called bubble point of the material, when the filter is wetted by the liquid. The bubble point is defined as the characteristic pressure at which the first bubble of air appears when a filter material is pressurized with air, while immersed just under the surface of the liquid. The bubble point effect is described in U.S. Pat. No. 3,007,334, dated Nov. 7, 1961, and makes it possible to determine the maximum pore size of filter elements, since the air pressure at the bubble point can be directly correlated with the pore size of the filter.

It is apparent that if a filter saturated with fluid is interposed in the line leading from a liquid supply to a patient, air cannot pass along the line beyond the filter, so long as the fluid pressure is below the bubble point of the filter. Such devices have therefore been proposed to prevent the accidental passage of air to patients. However, the problem with such devices is that although they block the passage of air they do not vent it, with the result that the air held back by the filter can cover the surface of the filter, restricting flow, or even blocking it, if the surface is completely covered with air, at the same time increasing the pressure drop across the filter, with the resultant danger that the bubble point of the filter can be reached sooner than expected, after which the blocked air can pass through virtually all at once. The presence of the filter also makes it impossible to clear the line of air, after the filter has once been wetted, and therefore the filter must be dried, before the line can be used again, so that it can be cleared of air before the next use. This, however, is a problem, particularly if the filter must be steam-sterilized or hot water-sanitized before use.

The problem is particularly troublesome with microporous filter material having pores of less than one micron in diameter. Such filters are intended to filter out harmful microorganisms from fluids, but in such filters, the pressure differential needed to force air through the filter wetted with liquid can be as high as 30 p.s.i.d., as a result of which complete filter blockage can result from the presence of air in sufficient quantities in the system to cover the surface of the filter.

The impermeability to gas of the wetted filter medium poses serious problems in many applications. Thus, prior to the administration of intravenous liquids, it is necessary to remove all air from the equipment.

A further difficulty with such filters has been the clumsy mode of connection to the supply of liquid to be administered intravenously and to the intravenous administration set or apparatus. The drip chamber assembly described in U.S. Pat. No. 3,557,786, for example, has tubing connections, which require special connectors at both inlet and outlet.

The design of the drip chamber poses another problem, hold-up and eventual loss of the liquid in the drip chamber, plus the flow delay arising from this hold-up during fluid administration.

Keedwell U.S. Pat. No. 3,520,416 patented July 14, 1970 provides microporous materials suitable for use as filter media that are capable of passing liquids at low differential pressure while at the same time passing gases even though the materials are wet with or even saturated with a liquid. This unusual characteristic is obtained by providing two kinds of pores through the material, one kind that are preferentially wetted by the liquid, and one kind that are not, and as a consequence do not absorb enough liquid to be plugged with liquid, and therefore are available for passage of gas therethrough.

Riely and Skyles U.S. Pat. No. 3,631,654, patented Jan. 4, 1972, propose to avoid the gas blockage problem by providing a gas purge device including a filter element that contains both liquid-wetted and liquid-repellent parts, interposed across and screening separate outlets for liquid and gas. The liquid-wetted parts will pass the liquid, and the liquid-repellent parts will not be wetted by liquid, and will therefore remain open for passage of gas therethrough. The liquid-wetted and liquid-repellent parts open into separate outlets, the outlet downstream of the liquid-repellent part being a gas outlet, and the outlet downstream of the liquid-wetted part being the delivery passage for gas-free liquid from the device. In this way, the device is capable of separating gases and liquids, and of either venting the gas or delivering it to a gas collection device, while at the same time providing a gas-free supply of liquid. Blockage of the system by the buildup of a gas lock is avoided, while at the same time the entrained gas is entirely eliminated from the liquid. Thus, the device of the invention is particularly adapted for medical applications, where air must be vented from the line, and must also be absolutely prevented from reaching a patient receiving an injection of the liquid. In a preferred embodiment, the filter employed has pores less than about 0.5 micron. If harmful microorganisms are to be filtered out from the fluid, the pores preferably should be less than about 0.3 micron, and then both the liquid and the gas passing through the device are sterilized at the same time. The device has the further advantage that the liquid-wetted or hydrophilic and liquid-repellent or hydrophobic parts can both be provided on the same filter element, thus facilitating servicing, and simplifying the construction.

The Riely and Skyles gas purge device comprises, in combination, a housing, an inlet in the housing for flow of fluid thereinto comprising gas and liquid, an outlet for delivery of liquid-free gas from the housing, and at least one filter element interposed across and screening both the gas and the liquid outlets. There is a liquid-repellent filter or part thereof interposed across and screening the gas outlet, and a liquid-wetted filter, or part thereof, interposed across and screening the liquid outlet, such that only gas can pass from the inlet through the filter into the gas outlet, and only liquid can pass from the inlet through the filter into the liquid outlet. Both the liquid-wetted and liquid-repellent filters preferably have a pore size less than about 0.3 micron, at which harmful microorganisms cannot pass through, and both are preferably portions of the same filter element. The housing and associated parts of the gas purge device are preferably made of plastic, and are bonded or fused together in a one-piece construction. The filter element can be fixed therein, so that the entire unit is disposed of when the element needs replacement, or can be removably positioned in the housing for easy replacement when needed.

This device is to be used in conjunction with a drip chamber of conventional type, and the problem is, that this requires two devices instead of one, with resultant increased expense.

A similar device is provided by Rosenberg U.S. Pat. No. 3,523,408, patented Aug. 11, 1970.

The Rosenberg gas separator comprises, in combination, a housing; a chamber in the housing of which chamber one wall comprises a filter material that is wetted by a liquid to be passed through the housing, and another wall comprises a filter material that is not wetted by the liquid passing through the housing, but in fact is liquid-repellent; an inlet in the housing for delivering fluid comprising gas and liquid to the chamber between the liquid-wetted and liquid-repellent filter materials; a liquid outlet in the housing on the opposite side of the liquid-wetted material; and a gas outlet in the housing on the opposite side of the liquid-repellent material. Both the liquid-wetted and the liquid-repellent materials preferably have a pore size less than about 0.3 micron, at which harmful microorganisms cannot pass therethrough. The housing and associated parts of the separator are preferably made of plastic, and are bonded or fused together in a one-piece construction.

An administration kit utilizing this type of gas separator device is described in U.S. Pat. No. 3,650,093 patented Mar. 27, 1972.

The vented filter spigot in accordance with the present invention combines all of these multiple vented spigot, gas filter, liquid filter and gas separator device systems into one, all included within a single spigot housing. The result is a vented spigot that ensures uninterrupted gravity feed of liquid from rigid-walled liquid supply containers, with a filtered air flow into the container via the spigot, a filter liquid flow from the container via the spigot, and a separation of any gas entrained with the liquid before delivery of the liquid from the container, either venting the separated gas or returning it to the container, according to the direction of gas flow through the vent. Moreover, the spigot is self-purging of any air contained in it initially, and aspirates air as required into the container via the vent, to prevent build up of a vacuum in the container automatically, as a consequence of being liquid-filled, and of liquid flow out from the container via the spigot.

While the vented spigot of the invention has these particular advantages when used with a rigid-walled supply container, it can also be used with flexible-walled containers. In such containers, aspiration of air is unnecessary to maintain continued liquid flow because the container collapses on itself as liquid is withdrawn. The spigot nonetheless separates and vents any gas entrained in liquid, and prevents air injection under pump-induced flow. The spigot is thus a truly universal spigot that can be used to advantage with all types of liquid supply containers.

The vented filter spigot in accordance with the invention comprises, in combination, a filter spigot housing; a filter chamber in the housing; an inlet and an outlet in the housing, the housing being arranged to have the inlet oriented up and the outlet oriented down when installed for liquid feed from a liquid supply for intravenous administration; the inlet being shaped for attachment to a supply of liquid in a rigid-walled container for intravenous administration, and the outlet being shaped for attachment to an intravenous liquid administration apparatus; a liquid-permeable filter that is gas-impermeable when filled with liquid disposed in the filter chamber in a manner so as to extend generally vertically when the inlet is oriented up, and across the line of fluid flow through the chamber from the inlet member to the outlet member so that all through flow must pass through the filter; and dividing the chamber into two generally vertically-extending portions, one upstream and one downstream of the filter; a vent in an uppermost portion of the housing when the inlet is oriented up in flow communication with the upstream portion of the filter chamber; and a liquid-impermeable gas-permeable filter disposed across the line of flow through the vent, so that all vent flow must pass through the filter, the filter restricting such flow to gas to which it is permeable; first and second passages in the housing putting the inlet into fluid flow communication with the filter chamber, the first passage opening into an upper part of the upstream portion of the filter chamber, and the second passage being longer than the first and opening into a lower part of the upstream portion of the filter chamber; whereby outflow of liquid via the filter chamber through the outlet aspirates air via the vent, liquid-impermeable gas-permeable filter and first passage into the container holding the supply of liquid, and makes it possible to maintain liquid flow from the container via the second passage to the outlet.

In a preferred embodiment, the spigot is provided with an inlet member having a spiked tip for piercing a supply container made of flexible or rigid plastic sheet or film, and forming a liquid-tight seal therewith, and an outlet member having a standard fitting, such as a spike socket, for attachment to an intravenous administration apparatus similarly equipped with a spike or other standard fitting that can enter the socket.

If the spigot is for gravity-feed use (as opposed to pump-fed intravenous administration) it is important that the housing be capable of being oriented with liquid inlet up and liquid outlet down, and with the vent in an upper portion of the housing well above the outlet, so that any gas separated from liquid can be vented and escape. The liquid-permeable filter and the filter chamber would then be oriented vertically, so that gas can rise along the filter to the top of the chamber, with the gas-permeable filter above the liquid-permeable filter at least adjacent the vent, and preferably along the top of the chamber.

It is also important that the first and second fluid passages intercommunicating the inlet with the filter chamber enter the top and bottom portions of the vertical filter chamber, respectively, the first at or above the level of the vent, and the second at or above the level of the outlet, and well below the level of the vent. This ensures aspiration of air via the vent and first passage, because of the greater length and weight of the column of liquid in the second passage as compared to the first, while liquid flow to the outlet proceeds via the second passage. This intercommunication of the inlet, fluid passages and filter chamber also causes the filter chamber to become liquid-filled automatically when flow starts from the liquid supply container, which purges the spigot of air and also returns any gas not vented to the container, where it replaces liquid drawn out, and joins air drawn in via the vent and first passage, thus preventing gas blockage of fluid flow delivered by the spigot.

A preferred embodiment of the vented filter spigot of the invention is illustrated in the drawings, in which:

FIG. 2 is a longitudinal sectional view taken along the line 2—2 of FIG. 1; and

FIG. 3 is a cross-sectional view taken along the line 3—3 of FIG. 1.

Figure 1:
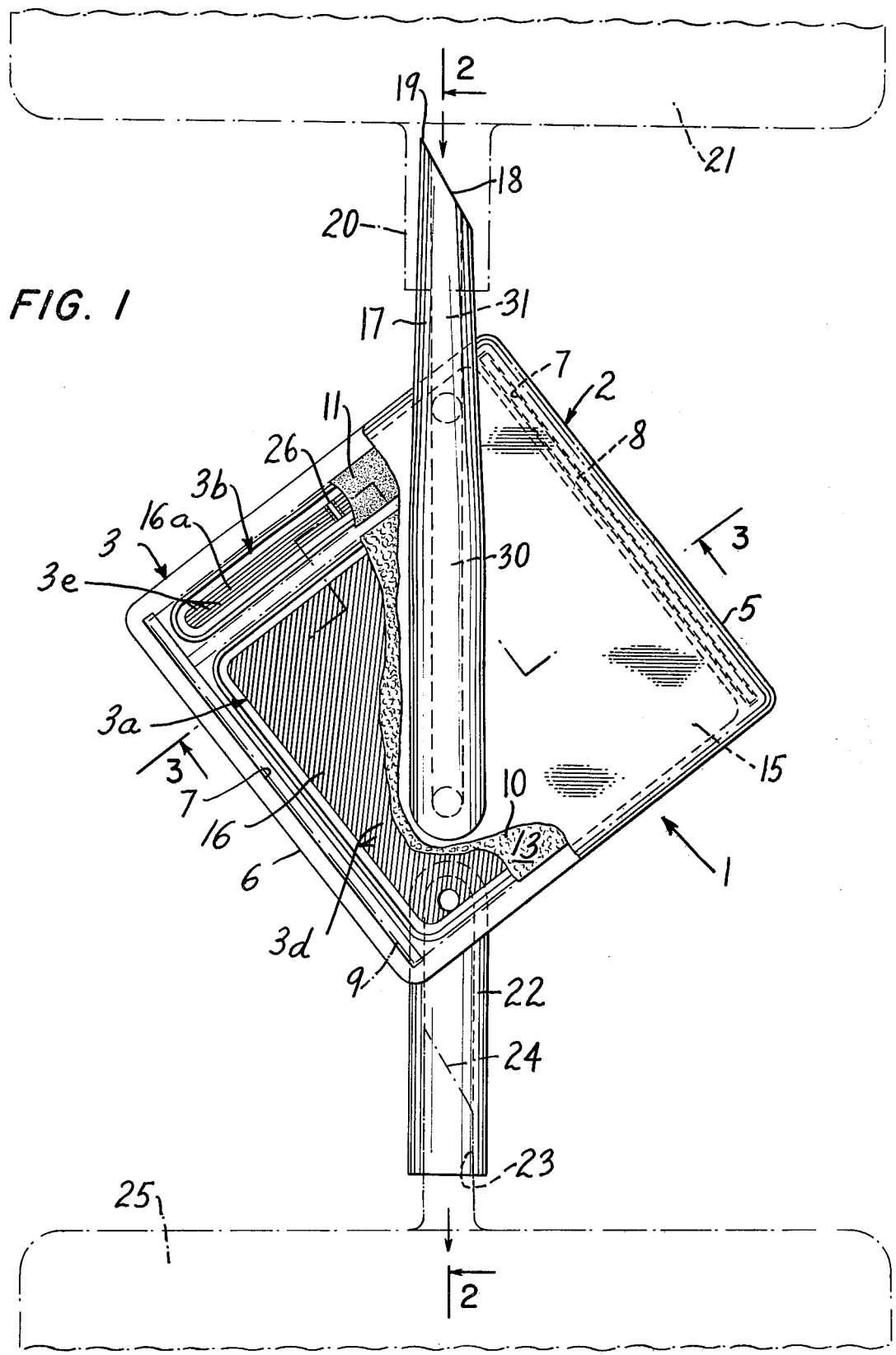
FIG. 1 represents a longitudinal section through a vented filter spigot of the invention, shown attached to a rigid-walled liquid supply container.

The spigot housing can be of either a rigid or a flexible construction. Each type of construction has certain advantages. A rigid construction, using rigid sheets or molded or cast plastic parts or tubing, or parts or tubing made of metal, makes it possible for the device to resist high internal fluid pressures up to the lowest bubble points of the filters used. The housing can also be made of flexible tubing or sheet material.

The spigot housing can be transparent, in which case the functioning of the device and the condition of the filter can be observed without dismantling the device. The filter that is employed serves to remove both gaseous and suspended solid material, such as dirt and other contaminants, either of which could lead to filter blockage.

It will be evident from the above that the spigot housing can be constructed of rigid or flexible plastic material that is also transparent, such as polyethylene, polypropylene, polymethyl methacrylate, polymethyl acrylate, polymethyl pentene-1, polyvinyl chloride, and vinyl chloride-vinylidene chloride copolymers. Translucent materials such as polypropylene, polyethylene, urea-formaldehyde and melamine-formaldehyde polymers can also be employed. Other plastic materials that are suitable include polystyrene, polyamides, polytetrafluoroethylene, polychlorotrifluoroethylene, polycarbonates, polyesters, phenol-formaldehyde resins, polyvinyl butyral, cellulose acetate, cellulose acetate-propionate, ethyl cellulose and polyoxymethylene resins.

Metal housings can be used. Suitable metals include stainless steel, aluminum, and stainless alloys, such as nickel, chromium, vanadium, molybdenum, and manganese alloys. The housing material should of course be inert to the fluids being processed.

The liquid-permeable gas-impermeable filter material is wetted preferentially by the liquid, and can have any desired pore size, according to the nature of the fluid being treated, and the nature of the contaminants, if any, to be removed. Since most filter materials are wetted by some liquids, and repel others, the material chosen for the filter will depend upon the fluid being processed.

In order to be effective in repelling and therefore not passing a gas, the liquid-wetted portion of the filter material should have a pore size of less than about 25 microns, and preferably less than about 3 microns.

In order to be effective in repelling and therefore not passing a liquid, the liquid-repellent gas-permeable filter material across the vent in the housing likewise should have a pore size of less than about 25 microns, and preferably less than about 3 microns. Thus, the same filter can easily serve as a substrate for both the filter and the porous member.

For bacteria removal purposes, as previously indicated, the pore size of both the liquid-permeable and gas-permeable filter materials should be less than about 0.3 micron, and preferably less than 0.2 micron. A filter material or porous member that has too large a pore size can have the pore size reduced by impregnation, or coating, or both, with particulate and/or fibrous material. Such materials and procedures are known.

Thus, there can be used as the liquid-repellent porous member woven or nonwoven textile materials made of cotton, jute, sisal, hemp, flax, linen, wood fiber, metal wire, such as stainless steel, copper and aluminum, plastic filaments (monofilaments and yarn) such as nylon, polyvinyl chloride, polyacrylonitrile, esters of terephthalic acid and ethylene glycol, cuprammonium rayon, acetate rayon, viscose rayon and polyvinylidene chloride, sintered composites made from metal powder or particles, such as stainless steel, copper, bronze, or Monel, or from plastic particles, such as polyvinyl chloride, nylon, polyethylene, polypropylene, polytetrafluoroethylene, and polyfluorotrichloroethylene; glass and ceramic materials; papers of various types, made up of celulose fibers, cellulose fluff, plastic fibers, such as polyvinyl chloride, cellulose acetate, polyvinylidene chloride, nylon, and any of the other plastic filaments mentioned above, taken singly or in any combination; and microporous sheets, such as synthetic resin and cellulose derivative membrane filters.

Impregnated and/or coated microporous filter sheet materials meeting these general requirements and that in particular can be made with less than 0.3 micron pores and thus are useful to prevent entry of harmful microorganisms include the microporous materials of U.S. Pat. No. 3,158,532 to Pall et al dated Nov. 24, 1964; No. 3,238,056 to Pall et al dated Mar. 1, 1966; No. 3,246,767 to Pall et al dated Apr. 19, 1966; and No. 3,353,682 to Pall et al dated Nov. 21, 1967. Also useful for this purpose are microporous ceramic filters and the microporous membrane filters described in U.S. Pat. No. 1,421,341 to Zsigmondy; No. 1,693,890 and No. 1,720,670 to Duclaux; No. 2,783,894 to Dovell; No. 2,864,777 to Robinson, and No. 2,944,017 to Cotton.

Liquid repellency in the gas-permeable filter is obtained, if the filter is of a material that is wetted by the liquid, by treatment of that portion of the material with a material that repels the liquid when disposed on the surfaces of the pore walls of the filter material. The repellent material can be applied from a solution or dispersion thereof, in a solvent or dispersant, which desirably includes a binder, to retain the repellent on the pore wall surfaces, unless the repellent is reactive therewith, and can bond itself thereto.

The application can be by printing, spraying, coating, impregnating, dipping, or by exposure to a vapor, such as that of a low boiling silicone compound. It is necessary to use a technique that results in thorough treatment of the entire length of the pores, from surface to surface of the filter material. This requires impregnation of the wall surfaces of the pores from end to end, best achieved by allowing the solution or dispersion of the repellent to flow into and through the pores in the treated zone, by capillarity or by pressure It will be appreciated that in nonwoven substrates, such as paper, nonwoven bats, and microporous layers formed by laydown from a fluid dispersion, the through pores that extend from one surface to another are composed of interconnected pores which are the interstices between the particulate material of which the material is made.

The amount of repellent that is required depends upon the effectiveness of the material as a repellent, and the volume of pores being treated. Usually less than 25% by weight of the volume being treated and preferably from 0.025% to 15% by weight of the volume being treated is sufficient.

The repellent is chosen according to the liquid suspending medium being filtered. It must repel such liquid, or be rendered so in situ on the pore surface.

For a hydrophobic or water-repellent surface, there can be used silicone resins and silicone oils of the general type $R_n$—Si—O—Si—$R_n$, where n is 1 or 2. n is 1 in the case of fluids, and n is 2 in the case of the solids, which contain crosslinks between chains. Mixtures containing species in which n is from 1 to 3 can also be used. R is a hydrocarbon group having from one to eighteen carbon atoms.

Also useful are the quaternary ammonium salt derivatives of silicone compounds described in U.S. Pat. No. 2,738,290, dated Mar. 13, 1956. These are substantive to cellulosic filter materials, as noted in the patent. Also, the hydrophobic oils and waxes can be used, in appropriate circumstances, where they can be made permanent.

If the filter material is liquid-repellent, and it is desired to make it liquid-wetted, it is advantageous to apply a liquid-wetting material thereto. The same treatment principles and proportions apply to liquid-wetted materials as to liquid-repellent materials. Typical wetting agents that are suitable are polyvinyl alcohol, alkyl aryl polyether alcohols, melamine formaldehyde resins, and the like. These wetting agents can be applied from a dispersion or emulsion. The vent and porous member that passes the gas being separated from the liquid is so placed in the housing that the gas can reach it. Inasmuch as gases normally rise, this means that at least a part of the liquid-repellent member is at an upper portion or wall of the housing. If the liquid-repellent material is confined to a lower portion of the housing, the air or the gas may not pass through it until an air pocket deep enough to reach the uppermost portion of the member has built up in the chamber. The building up of such a gas pocket is not a disadvantage, if the liquid-wetted filter material is still fully open to the passage of fluid, and is not covered by or immersed in the air or other gas pocket, but such a device may be position-sensitive. It is therefore less preferred, for some uses.

In their simplest construction, the liquid-permeable and gas-permeable filter elements have a flat surface, or substantially so. However, in order to increase the surface area of either or both filters, for use in a limited space, the filters can be curved, bowed inwardly against flow or outwardly in the direction of flow, and also can be corrugated. The filter can extend straight across the two outlets, if they are in-line, or in a Y-configuration, or it can be bent, say, in an L-shape, if the outlets are at right angles to each other, as in a T-housing, or in an in-line housing with the gas outlet in a wall of the through passage, upstream of the outlet. The filter can also be tubular, and extend all the way around the wall of the through passage in the liquid repellent portion, and have a liquid-wetted tip portion extending across the passage, as in a thimble.

For simplicity of construction, the spigot housing is best formed in two or three matching pieces, which when assembled define the interconnected through fluid passages, inlet and outlets, with the liquid-repellent filter material fixed across the gas outlet, and the liquid-wetted filter material fixed across the liquid outlet, and preferably parts of the same filter element. These parts can be separately molded, and then attached together, by bolts, or by heat-fusing, or by solvent-or adhesive-bonding. In the case of plastic materials, solvent-bonding is a preferred attachment technique, because it eliminates the presence of extraneous adhesives, does not affect transparency at the joints of a transparent housing, and is also leakproof.

The housing parts are constructed so that the filter materials contained therein are attached to the walls thereof across from the inlet and/or outlets, so that all fluid must pass through some part of the filter before it can emerge from the housing. If there are two housing parts, one housing part has a gas outlet or vent on the outside of the liquid-repellent porous member, and the same housing part has a liquid outlet communicating with the space on the outside of the liquid-wetted filter material. The housing thus has at least three openings, the inlet, and two outlets, one of which also serves as an air inlet for relieving vacuum in bottle, to which the fluid containing both gas and liquid is delivered, for separation of the gas therefrom and the opposite side of the liquid-repellent and liquid-wetted materials, respectively, being adapted to vent gas separated from the liquid, and to deliver liquid from which gas has been separated.

The two inlet passages leading to the upper and lower portions of the filter chamber can be formed with one (for example, passage 30 shown in FIG. 2) in one housing portion and the other (passage 31 shown in FIG. 2) in the housing portion carrying the vent or gas outlet and liquid outlet. The separating wall therebetween can be bonded in place on either housing part at the time or before the housing parts are attached together by any of the techniques described above. The filters (10 and 11, for example, in FIG. 2) can be attached in place to the housing part at the same time. Thus, the assembly is quite simple.

The square shape of the housing also facilitates attachment of the filter sheets to the housing part. If the housing parts are placed side by side, with the recesses for filter sheets 10, 11 abutting each other in adjacent parts, and in alignment, the filter sheets can be attached as continuous strips, and after attachment at the recesses the selvages can be cut off. Thus, a continuous assembly line manufacturing technique is possible for both filter sheets (10 and 11 in FIG. 2).

The device shown in the drawings illustrates one embodiment of this type of construction.

The vented filter spigot shown in FIGS. 1 to 3 has a spiot housing 1 of transparent rigid or semirigid plastic material, such as polyvinyl chloride, polystyrene or polycarbonate, polymethyl acrylate, polymethyl methacrylate, or polyvinylidene chloride; or of translucent material, such as polypropylene, polyethylene, or polyamide; or opaque, such as acrylonitrile-butadiene-styrene terpolymer, polystyrene, or polycarbonate. The housing is a flattened cube, in two portions 2, 3. Each housing portion 2, 3 is shallowly dished with outer peripheral flanges 5, 6. Portion 3 has peripheral slots 7 on two sides and portion 2 has peripheral ribs 8 extending into the slots 7. Portion 2 also has ribs on the flanges 5, which are sacrificially integrated and thus bonded to housing portion 3 at flange 6 to form the completed housing such as, for example, by ultrasonic welding or by use of an adhesive or mutual solvent; these ribs are accordingly not shown.

The slots 7 are deep enough to receive the end portion 9 of the filter sheet 10, and permit the flanges 5, 6 to be integrated together without interference by the edges 9.

The edges 9 of the filter sheet 10 are held in a fluid-tight seal to the portion 3 on the outer side of slots 7, and the filter sheet extends from end to end and side to side of the major part 3a of portion 3. The filter sheet 10 is liquid-wetted, and can for example be a microporous hydrophilic nylon membrane. Besides the sheet 10 and in the same plane, but extending only over part 3b of portion 3, is a liquid-repellent gas-permeable sheet 11, such as an expanded microporous polytetrafluoroethylene sheet. This sheet is also bonded to the portion 3 at its edges, in recess 3c.

The housing part 3a is ribbed, the ribs 3d extending diagonally across that part, while the part 3b is also ribbed, and ribs 3e extending parallel to the long sides of part 3b.

The housing encloses a filter chamber 13 and since the entire peripheries of the sheets 10, 11 are sealed to the housing portion 3, the filter 10 and sheet 11 accordingly divide the filter chamber 13 into an upstream portion 15, and a lower downstream portion 16, separated by wall 27 from upper downstream portion 16a.

The filter chamber is quite narrow, to keep volume as small as possible, and minimize the hold up volume of fluid in the housing at any given time. In use, the orientation of the housing as seen in FIG. 1 is such that the filter chamber is shaped like a double funnel, with narrow ends at top and bottom, for optimum fluid distribution in and collection from the filter chamber at top and bottom, respectively.

Opening into the upstream portion 15 of the chamber 13 is an inlet member 17 of generally tubular configuration, terminating in a spike 18 with a sharp tip 19 for penetration of the fitting 20 (shown in dashed lines) of a plastic reservoir or storage vessel 21 containing liquid for intravenous administration, and forming a leak-tight seal therewith when penetrated into the vessel.

On the other side of the filter 10, in the bottom of the downstream portion 16 of the filter chamber, is provided an outlet member 22, also generally of tubular configuration, and terminating in a socket 23, for reception of the corresponding spike 24 of an intravenous liquid administration kit 25, shown in dashed lines. Thus, liquid entering by gravity flow through the inlet member 17 passes down into chamber portion 15 and then must pass through the filter 10 in order to reach the outlet member 22 and the administration kit 25. The wall 27 closes off the portion 16 from the downstream portion 19 of the chamber 13.

Penetrating through the wall of the housing portion 3 and opening into the downstream portion 19 of the chamber 13 is a vent 26, closed off by liquid-repellent gas-permeable filter sheet 11, which extends along the top of chamber 13, to a point opposite the inlet member 17. Since this sheet is not wetted by the intravenous liquid being administered, since this is an aqueous fluid which wets hydrophilic materials but not hydrophobic materials, the pores of the polytetrafluoroethylene sheet are not penetrated by liquid, and therefore remain open for passage of gas therethrough at all times, which can accordingly escape via chamber portion 19 and vent 26 from the housing.

In contrast, the pores of the filter 10 are saturated with liquid, immediately that liquid fills the upstream chamber 15, with the result that under gravity flow administration, as shown, the filter 10 is not penetrated by gas, but blocks the passage of gas therethrough. As a result, any gas entering with the liquid through the inlet cannot pass through the filter 10, but since it can pass through the sheet 11, it escapes through the vent 26.

It will be noted that the spike 18 and socket 23 are at opposite corners of the housing 1. This means that the device when installed assumes the position shown in FIG. 1 in which the sheet 11 extends diagonally upward, and so is in a position to vent via vent 26 all gas rising to the top of chamber 15, aided by the ribs 3e. The ribs 3d are thus vertical, aiding in guiding liquid to outlet 22.

The inlet member 17 is connected with the filter chamber 13 by two passages, 30 and 31. Passage 30 extends to and enters the portion 15 of the chamber 13 near the bottom, and is longer than passage 31, which enters the portion 15 at the top, above the vent 26. This makes possible a separate flow of air into the supply container 21 via passage 31, while liquid flows out via passage 30.

Thus, in operation, after the spike 18 of the filter assembly has been pushed into the liquid supply vessel 21 at 20, as illustrated, liquid flows freely via both passages 30, 31 into the upstream chamber portion 15, and fills it completely. Liquid reaches and passes through the filter 10, and then enters the downstream chamber 16, whence it passes along the ribs 3d and leaves through the outlet member 22 and the socket 23 into the intravenous administration kit 25, where it is administered. Gas blocked from passage through the filter 10 travels upwardly through chamber portion 15, and escapes through the vent 26 via the liquid-repellent sheet 11. Thus, the spigot is self-purging of all air contained therein when liquid flow begins.

While this is going on, a vacuum is building up in the container 21, above the liquid level in the container. This vacuum is alleviated by air entering the vent 26, which passes into space 16a, through filter 11, and then upwardly via passage 31 into the container, bubbling up through the liquid. This air is filtered, and so contaminants are kept out of the container. This air flow continues until the container is emptied of liquid.

The vented filter spigot shown in the drawings and described above is useful to separate gases from liquids and to filter intravenous liquids from any kind of supply vessel in any type of medicinal and chemical application. It can, for instance, be used both to clear a line of air and to prevent the introduction of air and contaminants into a patient receiving an injection of any type of fluid medicament, such as a parenteral fluid, blood transfusions, blood plasma, intravenous feeding solutions, and the like. Such fluids can be delivered to a patient under gravity pressure, or under higher pressures, such as are encountered when the fluid delivery is effected by means of a syringe pump, and will prevent the introduction of air into the patient at all pressures below the bubble point of the liquid-wetted filter material that is used, both at the beginning of the introduction of the liquid, even when the line before the line before the separator contains air, and after delivery of fluid has exhausted the supply.

Having regard to the foregoing disclosure, the following is claimed as inventive and patentable embodiments thereof:

1. A vented filter spigot for gravity feed intravenous liquid administration, comprising a filter spigot housing; a filter chamber in the housing; an inlet and an outlet in the housing, the housing being arranged to have the inlet oriented up and the outlet oriented down when installed for liquid feed from a liquid supply for intravenous administration; the inlet being shaped for attachment to a supply of liquid in a rigid-walled container for intravaneous administration, and the outlet being shaped for attachment to an intravenous liquid administration apparatus; a liquid-permeable filter that is gas-impermeable when filled with liquid disposed in the filter chamber in a manner so as to extend generally vertically when the inlet is oriented up, and across the line of fluid flow through the chamber from the inlet to the outlet so that all through flow must pass through the filter; and dividing the chamber into two generally vertically-extending portions, one upstream and one downstream of the filter; a vent in an uppermost portion of the housing when the inlet is oriented up in flow communication with the upstream portion of the filter chamber; and a liquid-impermeable gas-permeable filter disposed across the line of flow through the vent, so that all vent flow must pass through the filter, the filter restricting such flow to gas to which it is permeable; first and second passages in the housing putting the inlet into fluid flow communication with the filter chamber, the first passage opening into an upper part of the upstream portion of the filter chamber, and the second passage being longer than the first and opening into a lower part of the upstream portion of the filter chamber; whereby outflow of liquid via the filter chamber through the outlet aspirates air via the vent, liquid-impermeable gas-permeable filter and first passage into the container holding the supply of liquid, and makes it possible to maintain liquid flow from the container via the second passage to the outlet.

2. A vented filter spigot according to claim 1, wherein each of the filters have an average pore size less than about 0.3 micron.

3. A vented filter spigot according to claim 1, wherein the housing and associated parts are made of transparent plastic.

4. A vented filter spigot according to claim 3, wherein the housing and any other plastic parts are bonded or fused together in a one-piece construction.

5. A vented filter spigot according to claim 1, wherein the inlet comprises an inlet member having a spiked end for piercing a wall of an intravenous liquid supply vessel.

6. A vented filter spigot according to claim 1, wherein the gas-permeable filter is a microporous membrane.

7. A vented filter spigot according to claim 1, wherein the outlet comprises an outlet member having a socket.

8. A vented filter spigot according to claim 1, wherein the wall of the housing portion downstream of each filter is ribbed with upwardly and downwardly extending ribs to facilitate flow of liquid to the outlet and gas to the vent.

9. A vented filter spigot according to claim 1, wherein the inlet comprises an inlet member carrying the first and second passages to the filter chamber.

10. A vented filter spigot according to claim 1, wherein the housing is in two portions, one portion including the inlet member and first and second passages to the filter chamber, and the other each filter, the gas vent and the outlet.

11. A vented filter spigot according to claim 10, wherein the two housing parts are attached together as one piece.

12. A vented filter spigot according to claim 11, wherein inlet comprises an inlet member having a spiked end for piercing a wall of an intravenous liquid supply vessel.

* * * * *